United States Patent
Lee et al.

(10) Patent No.: US 12,266,428 B2
(45) Date of Patent: *Apr. 1, 2025

(54) SYSTEM AND METHOD FOR DETERMINING SUBJECT CONDITIONS IN MOBILE HEALTH CLINICAL TRIALS

(71) Applicant: MEDIDATA SOLUTIONS, INC., New York, NY (US)

(72) Inventors: David Lee, New York, NY (US); Kara Dennis, New York, NY (US); John Savage, Fair Haven, NJ (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/473,009

(22) Filed: Sep. 22, 2023

(65) Prior Publication Data
US 2024/0013872 A1 Jan. 11, 2024

Related U.S. Application Data

(62) Division of application No. 14/630,259, filed on Feb. 24, 2015, now Pat. No. 11,804,287.
(Continued)

(51) Int. Cl.
*G16H 10/20* (2018.01)
*G06N 5/04* (2023.01)
(Continued)

(52) U.S. Cl.
CPC ............ *G16H 10/20* (2018.01); *G06N 5/04* (2013.01); *G06N 20/00* (2019.01); *G16H 50/20* (2018.01)

(58) Field of Classification Search
None
See application file for complete search history.

(56) References Cited

U.S. PATENT DOCUMENTS

| | | | |
|---|---|---|---|
| 7,899,225 B2 * | 3/2011 | Collins | A61B 5/4064 600/407 |
| 2006/0084848 A1 * | 4/2006 | Mitchnick | A61B 5/411 600/595 |

(Continued)

FOREIGN PATENT DOCUMENTS

| | | | | |
|---|---|---|---|---|
| CA | 2687587 A1 * | 12/2008 | ......... | A61B 5/14532 |
| WO | WO-2013036677 A1 * | 3/2013 | ......... | G06F 19/3418 |

OTHER PUBLICATIONS

Cipriano, "Optimal information collection for dynamic health care policy (Order No. 28122470)." Available from ProQuest Dissertations and Theses Professional. (2463197427). Retrieved from https://dialog.proquest.com/professional/docview/2463197427?accountid= 131444 (Year: 2013).

(Continued)

*Primary Examiner* — Rachel L. Porter
(74) *Attorney, Agent, or Firm* — STEPTOE LLP; Carl B. Wischhusen

(57) ABSTRACT

A method for calculating a subject's state or condition comprises integrating data that are captured from multiple sources, storing the integrated data in a first database, calculating time intervals in which to collect an optimal amount of data to predict the subject state, developing a predictive model using a recorded diary or electronic data capture information, testing the model against a portion of the captured data, and applying the predictive model to new data from other sources. The predictive model may determine a subject state that may be a digital bio-marker for a disease condition. A system for predicting subject state is also disclosed.

9 Claims, 10 Drawing Sheets

Related U.S. Application Data

(60) Provisional application No. 62/080,075, filed on Nov. 14, 2014.

(51) Int. Cl.
    *G06N 20/00*     (2019.01)
    *G16H 50/20*     (2018.01)

(56) References Cited

U.S. PATENT DOCUMENTS

| | | |
|---|---|---|
| 2006/0101072 A1 | 5/2006 | Busche et al. |
| 2006/0161403 A1 | 7/2006 | Jiang et al. |
| 2006/0184493 A1 | 8/2006 | Shiffman et al. |
| 2008/0147441 A1 | 6/2008 | Kil |
| 2011/0015865 A1 | 1/2011 | Rosenberg et al. |
| 2011/0078099 A1* | 3/2011 | Weston ............ G16B 40/20 706/12 |
| 2011/0112442 A1* | 5/2011 | Meger ............ A61B 5/7203 600/595 |
| 2011/0282169 A1 | 11/2011 | Grudic et al. |
| 2011/0289035 A1 | 11/2011 | Stojadinovic et al. |
| 2012/0250963 A1* | 10/2012 | Carroll ............ G16H 50/20 382/128 |
| 2013/0218053 A1 | 8/2013 | Kaiser et al. |
| 2013/0226613 A1 | 8/2013 | Srinivasan et al. |
| 2013/0262357 A1 | 10/2013 | Amarasingham et al. |
| 2013/0325498 A1 | 12/2013 | Muza, Jr. et al. |
| 2014/0279746 A1 | 9/2014 | De Bruin et al. |
| 2015/0038854 A1 | 2/2015 | Zhang et al. |
| 2015/0182130 A1 | 7/2015 | Utter, II |
| 2016/0085928 A1 | 3/2016 | Tsugo |
| 2016/0105402 A1 | 4/2016 | Soon-Shiong et al. |

OTHER PUBLICATIONS

International Search Report and Written Opinion, PCT/US2014/072483, Jun. 30, 2015.

* cited by examiner

SYSTEM AND METHOD FOR DETERMINING SUBJECT CONDITIONS IN MOBILE HEALTH CLINICAL TRIALS

CLAIM OF PRIORITY

This application is a divisional of U.S. patent application Ser. No. 14/630,259, filed on Feb. 24, 2015, which claims priority from U.S. Provisional Patent Application No. 62/080,075, filed on Nov. 14, 2014, each of which is incorporated by reference in its entirety.

BACKGROUND

Mobile health (mHealth) devices, such as activity and fitness trackers with sensors for monitoring physical activity, measure, collect, record and/or transmit data about a patient's (a/k/a a subject's) vital signs and other metrics (a personal metric). Such devices may each have one or more sensor for measuring one or more personal metrics, such as heart rate, respiratory rate, blood pressure, body or skin temperature, body mass, motion (speed, distance traveled, number of steps taken), blood oxygen saturation, and/or sleep quality or patterns, among other personal metrics. Such devices may be consumer- and/or medical-grade devices, including activity and fitness trackers (Fitbit®'s Force or Flex®, Jawbones Up™, Withings®, Aura™ or Pulse™ Nike's Nike+FuelBand®, BodyMedia®'s Link, Sony®'s SmartBand™, the Ssmart Dynamo, ActiGraph®'s Link), biosensors (such as those made by Vital Connect®'s HealthPatch®), wearable heart-rate monitoring chest straps (Holter monitor), pocket pedometers, etc. These devices typically monitor one or several personal metrics at a time, and the data from more than one device are generally not synchronized with data from other devices.

Figure 1A:
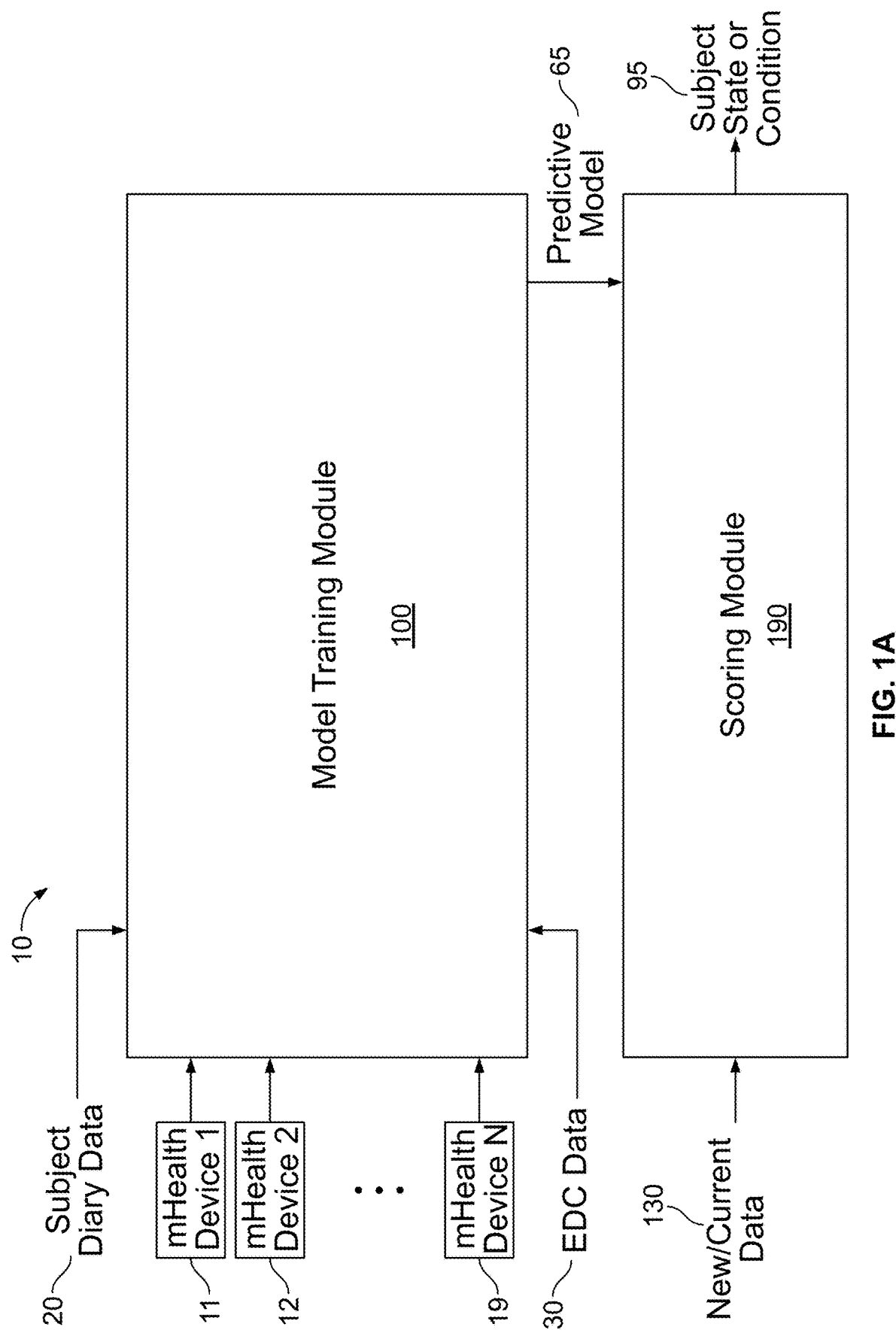
FIGS. 1A and 1B are block diagrams of a system for determining a subject's state or condition using data received from one or more mobile health devices, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Clinical trial patients (known as "subjects") may use one or more mobile health devices or other wearable devices (either or both referred to herein as "mHealth devices") to monitor personal data or metrics (e.g., heart rate, respiratory rate, blood pressure, body or skin temperature, body mass, motion (speed, distance traveled, number of steps taken), blood oxygen saturation, and/or sleep quality or patterns. However, mHealth devices do not objectively capture or determine the condition or state of a subject (alternatively called a "subject state" or a "subject condition"), which may include whether the subject is sleeping, exercising, or at work, or whether the subject is experiencing an adverse event, is in pain, or is suffering from a disease condition. Subject states can be indicative of disease or therapy progression, quality of life changes, and adverse events, and thus are valuable for clinical trial purposes.

Currently, subject states, as well as adverse events and disease conditions, must either be subjectively recorded manually by a patient (e.g., patient-reported outcomes or a patient diary) or somewhat more objectively observed by a health professional (requiring an in-patient setting and therefore an uncommon and limiting practice for clinical trial purposes). Patients often do not record their states or conditions at all or at the time the states or conditions are experienced, and as a result the reporting of subject states left to the subjective recollection of a patient creates a likelihood of misreporting (non-reporting or inaccurate reporting).

The inventors have developed a system for objectively calculating subject states in mHealth clinical trials. The system and related methods of the present invention include continuously and objectively collecting data from mHealth devices to determine subject states automatically and universally—across disparate subjects, subject states, and mHealth devices (device neutrality). Reliable and accurate subject state determinations as provided in this invention may provide clinical insights and endpoints that, where otherwise omitted from a regulatory (e.g., FDA) submission, may be clinically useful to judge, assess, and distinguish the drug, therapy, or device being tested in the clinical trial. The system may operate in real-time or delayed. Even where included in the regulatory submission, use of the invention may increase the completeness and accuracy of the data available for the drug, therapy, or device being tested, and also reduce the burden on patients participating in trials.

In one embodiment, the system may capture and analyze clinical trial subjects' data to determine the subjects' states, which may include sleep, exercise, adverse events, quality of life, etc. The system may receive subject data from multiple data sources, including mHealth devices. The data may come from a single device having multiple sensors, as well as multiple devices each having one or more sensors.

For example, sensors may be used to obtain body or skin temperature and heart rate, and accelerometers may be used to monitor physical activity and movement. As such, the system may integrate data from multiple sources (whether from one or multiple devices, e.g., if there is more than one sensor on a single device) regarding a particular subject in a clinical trial, and may also generate the particular intervals for which the data should be collected to classify subject state or condition.

As one non-limiting example of the determination of a subject state, a patient may experience an adverse event, such as intense pain. The patient's heart rate may increase, body temperature may decrease (due to sweating), and body movement relative to the patient's usual movement may also decrease. Heart rate, body temperature, and body movement data may each be obtained from separate mHealth devices, and/or sensors on one or more such devices. Analysis of all three integrated types of data may allow for determination of the state of that patient (adverse event), even where the patient himself did not report the intense pain event.

Integrated data may be used to generate a predictive classification model for accurate and reliable prediction of subject state. In some embodiments, the system may use a classification tree to segment or partition the data received from multiple sensors and/or data sources. The system may objectively classify the states of patient activity, well-being, adverse events, and/or disease condition by using machine-learning and other types of algorithms. Machine-learning algorithms may also be used to optimize the particular devices and their data to be used in future clinical trials with regard to subject state. The system may also objectively classify the patient activity states and/or disease condition using algorithms generated by statistical analysis (statistical modeling or statistical learning) and processing of subject states and conditions.

The system may transform raw mHealth data from one or multiple mHealth devices into usable and novel covariates/predictors that may be used for clinical trial analysis. The sampling times associated with the capture of the combined data may be different for each individual device or type of data. Accordingly, the system may normalize the data so that it may be combined to generate a predictive model.

The system and methods may be used to accurately, objectively, and quantitatively measure quality-of-life factors, adverse events, and/or otherwise omitted clinical variables (data) for the clinical evaluation of tested drugs, therapies, etc. Much quality-of-life data, such as related to movement (injuries, rheumatoid arthritis), quality of sleep, anxiety, and discomfort are not typically—if ever—available for drug and therapy evaluation in many therapeutic areas.

The system may also use devices with real-time transmission of data to monitor subjects to calculate subject states, conditions, and adverse events. Once the system has identified a predictive model, the system may be used to record states that a subject may not manually record or measure, or may not be aware of, such as whether the subject is stressed, rushed, experiencing worse arthritis, in pain, and/or is asleep (including in deep sleep or dreaming). The system may be also used as an alert to help capture additional data from a patient. For example, in collecting data necessary to determine a subject state of intense pain (e.g., one or more of heart rate (BPM), blood pressure, and movement data), even after the system has identified a predictive model for determining that state, the system may in addition ask the patient to confirm or describe the pain being experienced.

In one embodiment, the system may separate captured data into a training set of data and a test set of data, and a predictive model may be built solely with the training set of data. An "answer key," or objective subject states established by patient reported outcomes or third-party observation, may be associated with the captured data. The amount of data that may be separated into the training set and the test set may be customized or configurable. As described further herein, once the system dynamically generates a predictive model for determining subject states using the training set of data, the system may evaluate the accuracy of that generated predictive model by comparing generated predictive subject state against the actual subject state in the "answer key" contained in the test set of data.

A subject state may be represented as a function of multiple variables. For example, a patient's state (subject state) Y, which may refer to sleep, exercise, an adverse event such as vomiting, fatigue, pain, etc., may be represented as a function of variable X (in general according to the equation $Y=f(X)$), where X represents clinical data such as heart rate, ECG, body temperature, skin temperature, displacement (movement), blood pressure, etc. The use of more X variables by the system may improve the accuracy of the generated predictive model. As one example, an indication of vomiting may be calculated using an mHealth device having a body temperature sensor (body temperature being an X variable). Additional indications of vomiting, as opposed to body temperature rising due to exercise, may be derived from other sensors (from the same or another mHealth device) providing heart rate and gyroscopic or accelerometer data. Use of all three variables may provide a more accurate determination of the "vomiting." The system may also determine the optimal number of variables necessary to accurately predict a patient's state or condition. In the vomiting example, body temperature data may be revealed to be not as predictive as heart rate and gyroscopic data, and the predictive model may discontinue using that variable.

The system generated predictive model may use tree models such as a classification and regression tree (CART), random forests, or gradient boosting machine; statistical models, such as a linear regression or multinomial regression model; and/or machine-learning models, such as a support vector machine. In one embodiment, the system may generate a predictive model where Y may be a bio-marker for a disease condition. In other embodiments, such digital bio-markers and patient state algorithms may serve as proxies for, and thereby supplement, augment or replace, traditional clinical procedures and clinical endpoints.

Figure 1B:
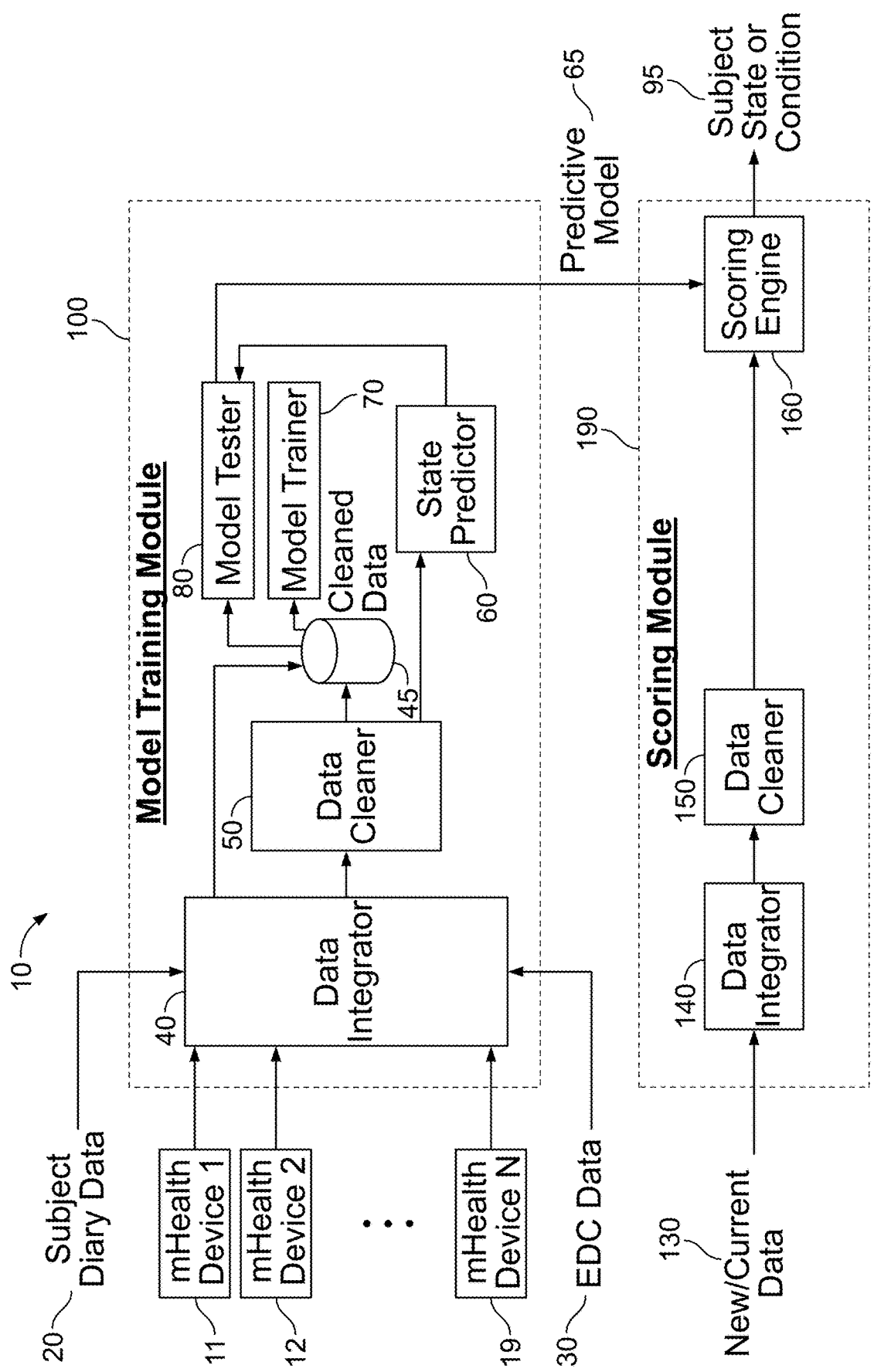

Reference is now made to FIGS. 1A and 1B, which are block diagrams of a system 10 for determining a subject's state or condition using data received from multiple mobile health devices 11, 12, . . . 19. System 10 includes model training module 100 and scoring module 190.

FIG. 1B shows these modules in more detail. Model training module 100 includes data integrator 40, database 45, data cleaner 50, and state predictor 60. Model training module 100 may capture data from multiple mHealth devices 11, 12, . . . 19. Data integrator 40 may integrate the captured data and the integrated data may be stored in database 45. Model training module 100 may calculate specific time intervals to collect an optimal amount of data from external mHealth devices 11, 12, . . . 19 to predict a subject's state or condition. Similarly, model training module 100 may select one or more optimal data sources to be used to determine a subject's state or condition 95.

Model training module 100 may partition the integrated data by classifying a combination of ranges of values for the variables associated with the captured data that optimally predicts the subject's state. This predictive classification model may be used by model training module 100 to determine or predict the subject's state 95. Model training module 100 may use machine learning and/or statistical analysis to process the data. The generated predictive model may be stored in a database.

The data from mHealth devices 11, 12, . . . 19, along with subject diary data 20 (if any) may be input to data integrator 40, after which data cleaner 50 may use one or more algorithms to clean the integrated data. Cleaning the data may include identifying and remediating univariate and multivariate outliers, reducing the noise in the data, e.g., by smoothing the data, by averaging the data over longer time periods than the data is sampled, or other signal processing. With respect to a heart rate (ECG) signal such as a QRS complex, the heart rate signal may be calculated as an R-R interval, and other intervals may be calculated, such as Q-T interval.

Model training module 100 may also include a supervised learning capability to develop or train the predictive model. Subject diary (or third-party observer) data 20 and/or EDC (electronic data capture) data 30 may input subject state or condition data to be used to train model training module 100. Subject diary data 20 may comprise data that a subject manually records in a diary or journal, listing the subject's state at specific points in time. The states may include how the subject is feeling, whether the subject is experiencing an adverse event (headache, nausea, vomiting, pain, etc.), how severe the adverse event is, whether the subject is sleeping (e.g., when the subject went to sleep and when the subject awoke), whether the subject is working, exercising, going out at night, eating, at rest (e.g., watching TV, reading), etc. Typically EDC data comprise clinical data from a clinical trial in which the subject is participating and show the subject's condition at the relevant timepoints. These data may include health data, such as heart rate, blood pressure, or lab data (e.g., blood and/or urine analysis), demographic data, doctor or medical assessments, or other data collected during a clinical trial.

In one supervised learning embodiment, subject diary data 20 and/or EDC data 30 may be integrated or synchronized with mHealth device data from devices 11, 12, . . . 19, and the integrated data are cleaned in data cleaner 50. The cleaned data are then transmitted to database 45, from which some are transmitted to model trainer and some are transmitted to model tester 80. Model trainer 70 may then use classification, regression, or other statistical or machine-language algorithms to develop a predictive model, which may then be sent to state predictor 60 and the results tested in model tester 80. If the results of the test are satisfactory, the predictive model may be stored, and the tested predictive model may be used to determine subject state or condition 95 via scoring module 190, as described below. If the results are unsatisfactory or if not satisfactory enough, the results may be fed back to modify the model or more data will be collected to raise the confidence level of the results.

Scoring module 190 takes new/current data 130, integrates the data in integrator 140, cleans the data in data cleaner 150, and then applies predictive model using scoring engine 160 to determine subject state or condition 95.

Because different mHealth devices or sensors track different variables, depending on the subject state being predicted, some devices or combinations of devices may prove better predictors than others. In that case, the model can determine which of the devices or device combinations performs better, and model training module 100 may select one or more of these optimal devices or device combinations to be used to determine a subject's state or condition.

The parts and blocks shown in FIGS. 1A and 1B are examples of parts that may comprise system 10, and do not limit the parts or modules that may be included in or connected to or associated with system 10. As indicated by the ellipsis on the left side of the figure, three mHealth devices are shown, but there may be more than three. Alternatively, there may be a single mHealth device that has multiple sensors and provides multiple data inputs. There may not always be subject diary data 20 and/or EDC data 30. And although a single database 45 is shown, there may be multiple databases storing different or the same types of data.

Figure 2:
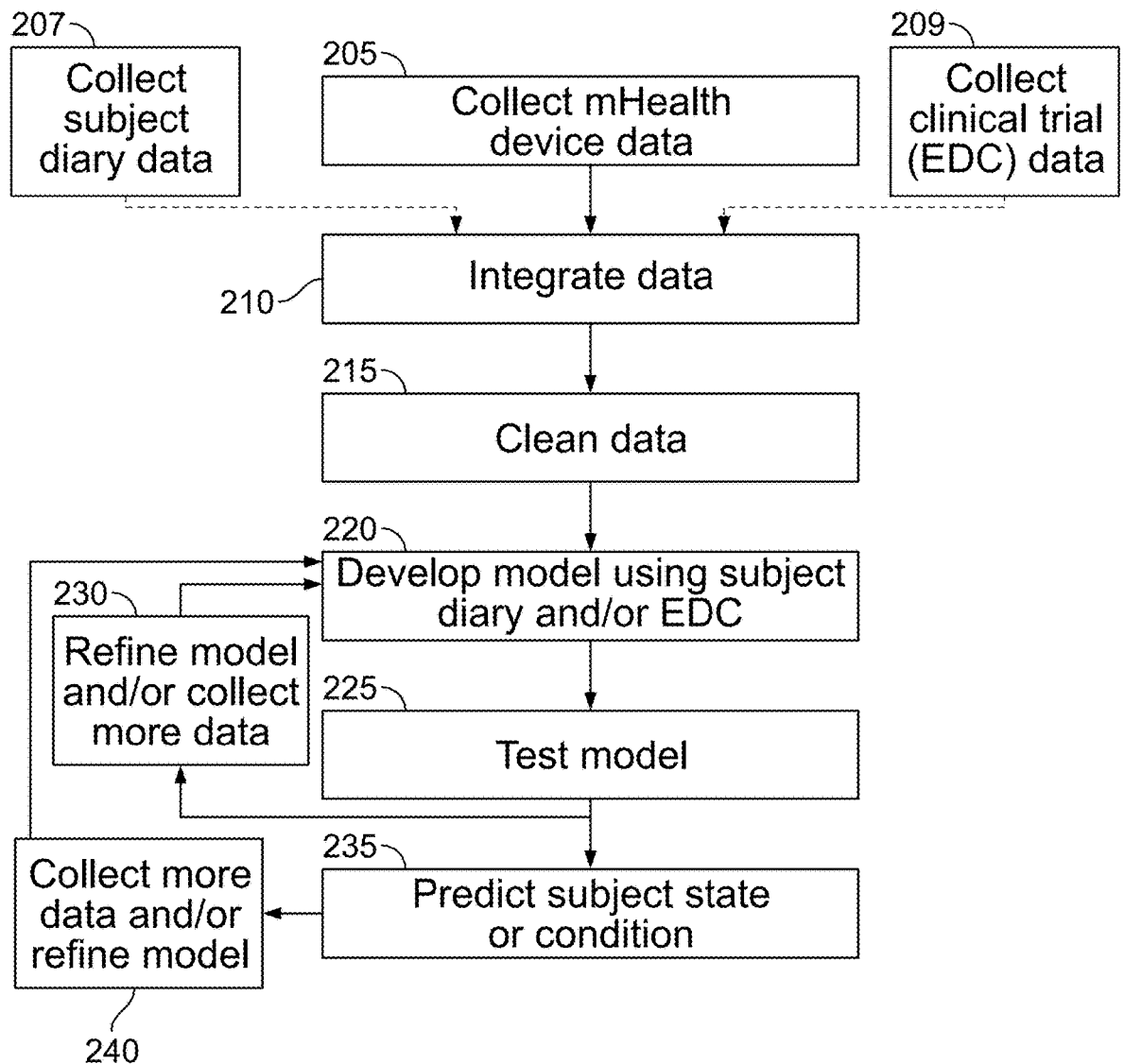
FIG. 2 is a flowchart illustrating the general operation of the system of FIG. 1 for determining a subject's state or condition using data received from one or more mobile health devices, according to an embodiment of the present invention.

FIG. 2 is a flowchart illustrating the general operation of system 10 for determining or calculating a subject's state or condition using data received from multiple mobile health devices. In operation 205, system 10 may collect data from mHealth devices 11, 12, . . . 19, and may integrate the data in operation 210. In supervised learning embodiments, system 10 may collect data 20 from a subject diary (or a third-party observer, e.g., a nurse or assistant or family member who records data for a subject) in operation 207 and/or collect clinical trial and/or EDC data 30 in operation 209. The integrated data may be associated with multiple variables that may be evaluated to predict a subject's state or condition. In operation 215, the integrated data may be cleaned as described above by data cleaner 50. In operation 220, the cleaned data may be used to develop a predictive model using the diary data 20 and/or EDC data 30. The model may be developed using statistical or machine-learning methods or algorithms. In operation 225, the model may be tested and if the results are satisfactory, the model may be used in operation 235 to predict a subject's state or condition. If the results are not satisfactory enough, the flow goes back to operation 220 via operation 230 to refine the model and/or collect more data. Even if the model is satisfactory and is used to predict the subject's state or condition in operation 235, there may be a feedback to operation 220 via operation 240 to acquire more data or refine the model further.

Figure 3:
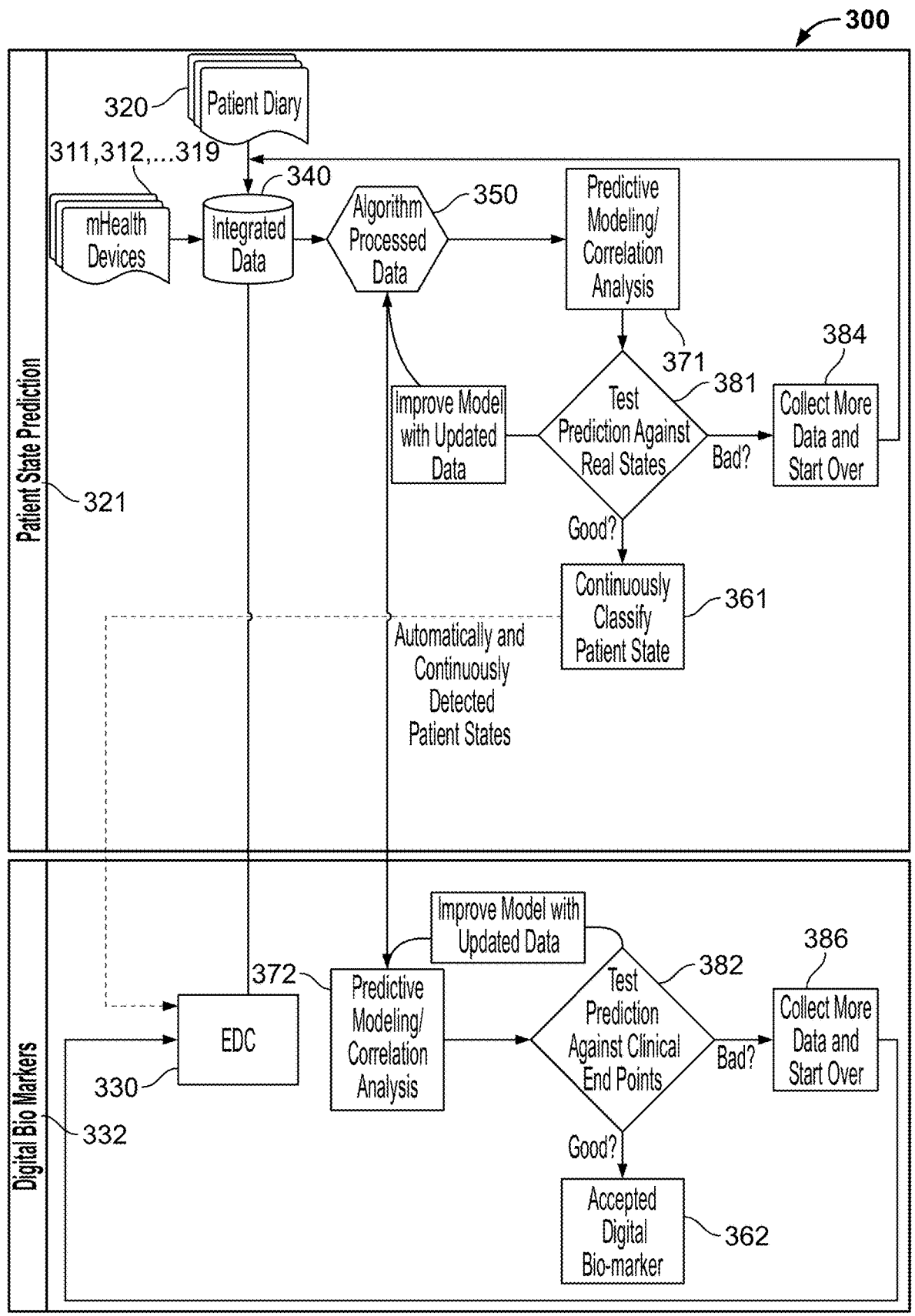
FIG. 3 is a flow diagram illustrating the flow and processing of data for predicting a subject's state or condition using data received from one or more mobile health devices, according to an embodiment of the present invention.

FIG. 3 illustrates the flow and processing of data in a system 300 for predicting a subject's state or condition using data received from multiple mobile health devices, according to an embodiment of the present invention. System 300 is similar to system 10, but more specific in certain places. System 300 includes block 321, which may facilitate subject state prediction, and block 332, which may facilitate establishing new digital bio-markers or other indications of a subject's disease condition or response to therapy. System 300 may capture and integrate data from mHealth devices 311, 312, . . . 319 and subject diary data 320 that may be manually provided by a patient. mHealth device data may include heart rate, steps taken, respiratory rate, ECG, body temperature, skin temperature, etc. Subject diary data 320 may relate to a subject's sleeping, exercising, pain and stress, and/or adverse event experience, such as vomiting. Integrated data 340 may be stored in a database.

System 300 may clean the integrated data to generate algorithm processed data 350. For example, the data may be partitioned by classifying a combination of ranges of values for the variables associated with the captured data that optimally predicts the subject's state. System 300 may normalize the data to reduce noise, and may use signal processing algorithms to generate specific time intervals for collecting an optimal amount of data to predict a state of a patient. System 300 may then generate a predictive model.

Figure 4A:
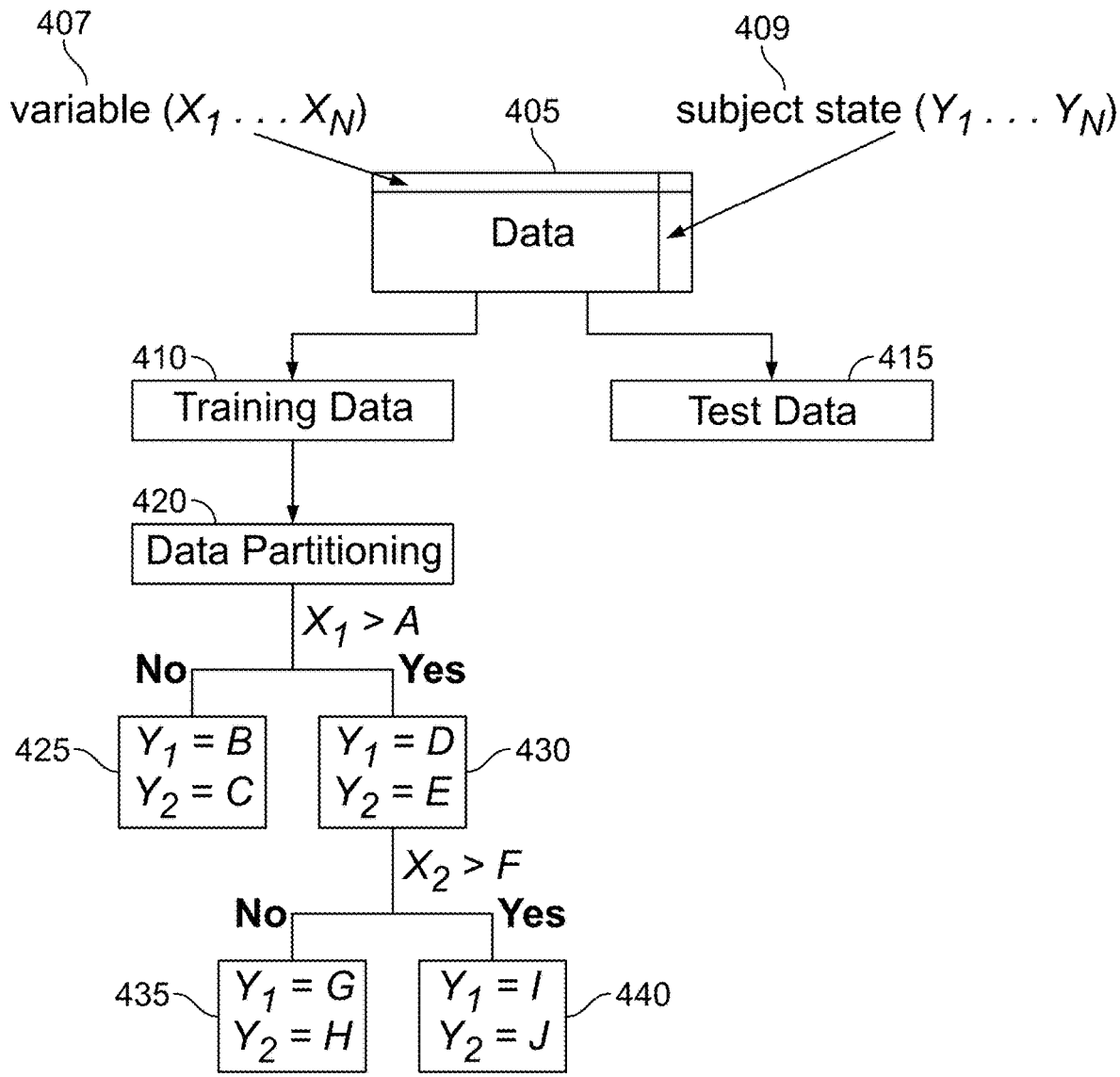
FIGS. 4A-4C are flow diagrams illustrating the partitioning of integrated data by classifying a range of values for each of the variables to optimally predict the subject's state or condition, according to embodiments of the present invention.
Figure 4B:
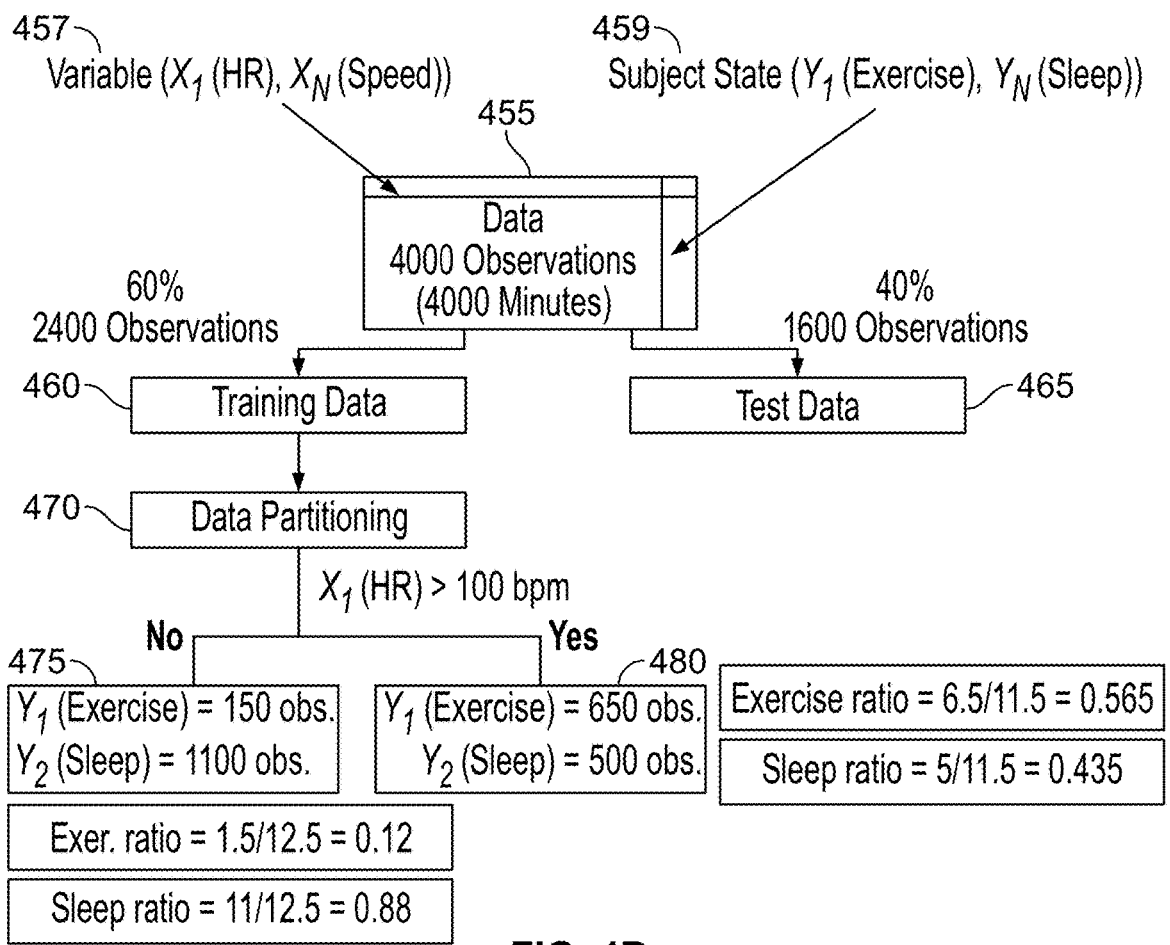
Figure 4C:
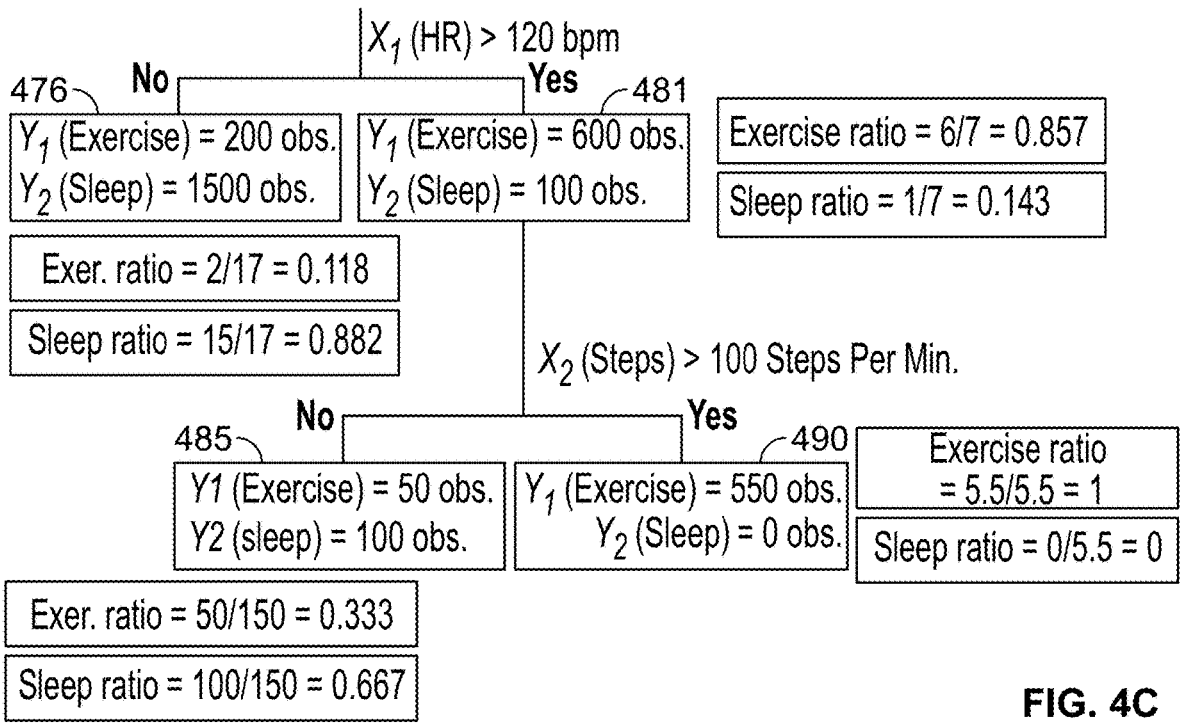

System 300 may perform predictive modeling and correlation analysis 371 on the captured data. If a predictive model has not yet been developed, one way to develop such a model is shown in FIGS. 4A-4C, which illustrate the partitioning of integrated data by system 300 by classifying a range of values for each of the variables to optimally predict the subject's state or condition. In FIG. 4A, data 405 captured by system 300 may comprise multiple data entries and each data entry may be associated with a variable 407 ($X_1 \ldots X_N$) (or a set of variables) and a subject state 409 ($Y_1 \ldots Y_M$). System 300 may separate the captured data 405 into a set of training data 410 and a set of test data 415. The percentages of the total amount of captured data 405 to be separated into training data 410 and test data 415 may be configurable, for example, 50% of the data goes into each set, or perhaps 60% goes into the training data and 40% into the testing data. The data in each set may be randomly selected in order to ensure the independence of the training and test data sets.

System 300 may use a classification tree 420 to partition the training data set. One example of a classification tree is CART—a classification and regression tree. For example, for a particular variable $X_1$, a particular range of data, $X_1 > A$ may be used to classify the data according to particular states $Y_1$, $Y_2$. System 300 may compute a ratio between state $Y_1$ and $Y_2$ (or between $Y_1$ and $Y_1 + Y_2$) and for data where $X_1$ is not $> A$ (see 425), and where data for $X_1$ is $> A$ (see 430). To classify a subject state based on a particular variable X, system 300 may calculate a range for which the ratio between the states $Y_1$ to $Y_2$(B to C, 425 and D to E, 430) is maximized. System 300 may apply this partitioning with respect to another variable $X_2$, and may compute a ratio between state $Y_1$ and $Y_2$ for data where $X_2$ is not $> F$ (see 435, G to H), and where data for $X_2$ is $> F$ (see 440, I to J), to generate an optimal range.

An example of the general modeling of FIG. 4A is shown in FIG. 4B. Assume data set 455 comprises 4000 observations (which would comprise 4000 minutes, if there is one observation per minute), 60% of which (2400) are randomly allocated to the training set and 40% of which (1600) are randomly allocated to the test set. There may be two X-variables 457, e.g., heart rate and speed, and two subject states 459, e.g., exercise and sleep. Looking at only one variable initially, for example, =heart rate, and both subject states, $Y_1$=exercise and Y 2=sleep, the system will take various values of $X_1$ and test those against the data to produce the best outcome ratios. Also assume that of the 2400 observations, 800 are allocated to exercise and 1600 are allocated to sleep as recorded in the subject diary.

The system may test HR>100 bpm. For the "yes" side of the tree (box 480), there may be 650 cases for exercise and 500 for sleep, so the exercise ratio is 650/1150=0.565 and the sleep ratio is 500/1150=0.435. For the "no" side of the tree (box 475), there may be 150 cases for exercise and 1100 for sleep, so the exercise ratio is 150/1250=0.12 and the sleep ratio is 1100/1250=0.88.

Next, the system may test HR>120 bpm, as shown in FIG. 4C. For the "yes" side of the tree (box 481), there may be 600 cases for exercise and 100 for sleep, so the exercise ratio is 600/700=0.857 and the sleep ratio is 100/700=0.143. For the "no" side of the tree (box 476), there may be 200 cases for exercise and 1500 for sleep, so the exercise ratio is 200/1700=0.118 and the sleep ratio is 1500/1700=0.882.

Based on these two tests of heart rate, 100 bpm and 120 bpm, 120 bpm provides a better indication of exercise than does 100 bpm because the 120 bpm "yes" side ratio (0.857) is higher than the 100 bpm "yes" side ratio (0.565). The system will test all practical values (or a range of values set by a user) of heart rate to determine the optimum heart rate decision point for determining the exercise and sleep states.

To improve the classification, a second variable, e.g., $X_2$=speed (in steps per minute), may be examined, as shown in FIG. 4C in the tree below box 481. Different speeds may be tested for each of the two subject states. As part of the example, if the optimum heart rate decision point was 120 bpm, yielding 600 exercise cases and 100 sleep cases, these cases may be further divided based on speed. Thus, it may be calculated that $X_2 > 100$ steps per minute yields 550 exercise cases and 0 sleep cases (box 490), whereas $X_2 < 100$ steps per minute yields 50 exercise cases and 100 sleep cases (box 485). Again, the speed decision point may be varied to arrive at the optimum point for determining the exercise and sleep subject states.

The system may objectively classify the states of patient activity and well-being, and/or adverse events by using algorithms that may be generated by machine-learning. Additionally, the system may use the machine-learning algorithms to define a subject's state or condition and to optimize and select which data and device(s) should be used to most accurately classify a state or condition and, as such, the system may be used to optimize the particular mHealth devices for a given clinical trial.

The predictive model developed in 371 may then be tested in 381 using the test data 435 to determine how well the model works. If the results are not satisfactory, for example, the model was only 75% correct (such level of correctness being configurable), the model may be improved with updated or additional data 384 or by using and testing a different model, and the process begun again.

If the results are satisfactory, the model may be used to continuously classify subject state in 361. In such embodiments where subject diary information or third-party observer data 320 is not available for a particular subject state (such as sleep, exercise, adverse event, etc.), the mHealth device data as analyzed by the satisfactory predictive model may be used to determine the subject's state. Testing the predictive model against real (known) states 381 may provide the basis for identifying and validating digital bio-markers, that is, sufficiently reliable clinical endpoints for purposes of the evaluation of the drug, therapy or device being tested in the clinical trial. One example of such a digital bio-marker may be limping. If it is empirically proven that limping is correlated with a health condition, for example, stroke recovery, and limping is a subject state that can be reliably classified by a predictive modeling/correlation analysis (such as shown in 372 in FIG. 3), this could be deemed a "digital bio-marker" for stroke recovery. The establishment of bio-markers expedites clinical trials so that identification of currently unknown digital bio-markers could transform the industry's pace of scientific discovery or medical breakthroughs. (The alternative to using a predictive bio-marker is to wait for a condition to progress to a clinical endpoint, such as death.)

mHealth data may be used to supplement, augment or replace clinical endpoints or measures. Digital bio-markers, based on mHealth data, can be used instead of or in addition to traditional clinical measurements or clinical endpoints in a clinical trial's study design or clinical protocol. Where digital bio-markers supplement, augment or replace traditional clinical procedures or endpoints, the efficiency of the clinical trial may be increased, and/or the cost and burden on patients may be decreased. For example, the clinical procedure of a six-minute walk test may be supplemented or replaced by a digital bio-marker, established by the present invention, correlated with mobility, exercise capacity, or other clinical endpoints. The use of such a digital bio-marker would decrease the burden to the subject and the time and cost to trial personnel for administering the six-minute walk test. In addition, because mHealth data is more objective, continuous and complete (e.g., gathered 24 hours a day, seven days a week rather than a snapshot in time), mHealth data or digital bio-markers may provide new information that ordinarily could or would not be collected (e.g., sleep data) in a clinical trial, and may improve clinical insights and outcomes.

Block 332 in FIG. 3 shows how system 300 may facilitate the prediction of digital bio-markers or other indications of a subject's disease condition. In this case EDC data may be used to train the system so that it can determine a bio-marker and predict a subject's condition—the EDC data provides the links between the bio-markers and the conditions in the same way that the subject diary provides the links between subject's activity and subject state. Thus, system 300 may capture and integrate data from EDC system 330 (including lab data, vitals, demographics, etc.). After EDC data are integrated (340) and cleaned (350), predictive modeling/correlation analysis 372 may be used to identify digital signals related to (and/or predictive of) disease progression and health improvement. For example, an improvement in Q-T interval may signal less susceptibility to ventricular arrhythmias or atrial or ventricular fibrillation, a better sleep pattern may indicate improvement in patient health, and the ability to walk less may be correlated to an increase in tumor size. In the digital bio-marker context, system 300 may use the generated predictive model to process data to test that predictive model against clinical endpoints 382 to determine the validity of digital bio-marker 362. System 300 may also determine whether more data need to be collected and re-processed 386 in order to more accurately identify and validate a digital bio-marker. As system 300 receives updated data, the predictive model may be improved and system 300 may automatically and continuously classify a digital bio-marker.

Besides the operations shown in FIGS. 2, 3, and 4, other operations or series of operations are contemplated to predict the state of a subject based on mobile health data. Subsidiary calculations or determinations may need to be made in order to carry out the operations shown in the flowcharts. Moreover, the actual orders of the operations in the flow diagrams are not indicated to be limiting, and the operations may be performed in any practical order.

In one example of how the present invention may operate, a test was run and data aggregated and exported from five mHealth devices simultaneously over a three-day period. The mHealth devices included four ActiGraph and one Vital Connect mHealth devices. The ActiGraph devices were placed on the subject's two ankles and two wrists, and the Vital Connect device monitored the ECG signal and other vital parameters. Each ActiGraph device monitored twelve variables and provided about 5000 observations (20,000 observations in total), and the four devices' data were aggregated and exported in 60-second epochs. The Vital Connect device sampled 8 variables over 100 times per second, resulting in about 49 million observations. These data were aggregated to 60-second epochs, reducing the number of observations to about 5000. When combined, the integrated data set included 54 variables and over 4000 observations at 60-second intervals.

Figure 5A:
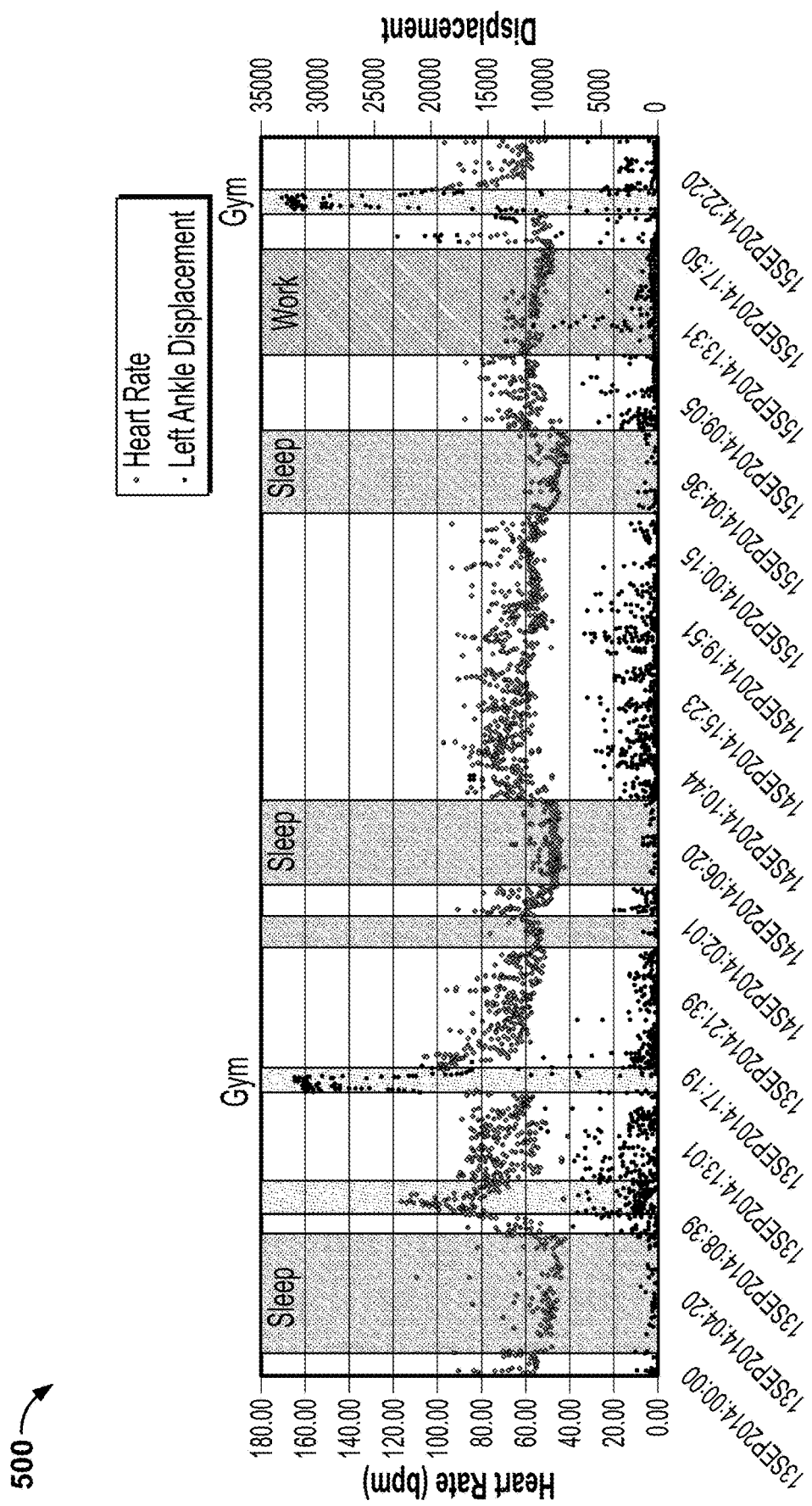
FIGS. 5A and 5B are graphs showing integrated data captured from multiple sensors during the experiment conducted according to an embodiment of the present invention.

The subject kept a diary as to when he was sleeping, working, and exercising (at the gym). Data from all four ActiGraph devices and the Vital Connect device were integrated with the subject's diary data and a predictive model was developed using CART and tested. FIG. 5A is a graph 500 of the integrated data captured from the left ankle ActiGraph device and the Vital Connect device. Heart rate is shown on the left axis and ankle displacement is shown on the right axis. These data are superimposed on the three subject states recorded in the subject diary during the three-day trial. FIG. another graph of the integrated data captured from the ActiGraph device and Vital Connect devices. Heart rate, steps per minute, and respiration per minute are shown. These data are superimposed on two subject states recorded in the subject diary during the three-day trial.

Figure 6A:
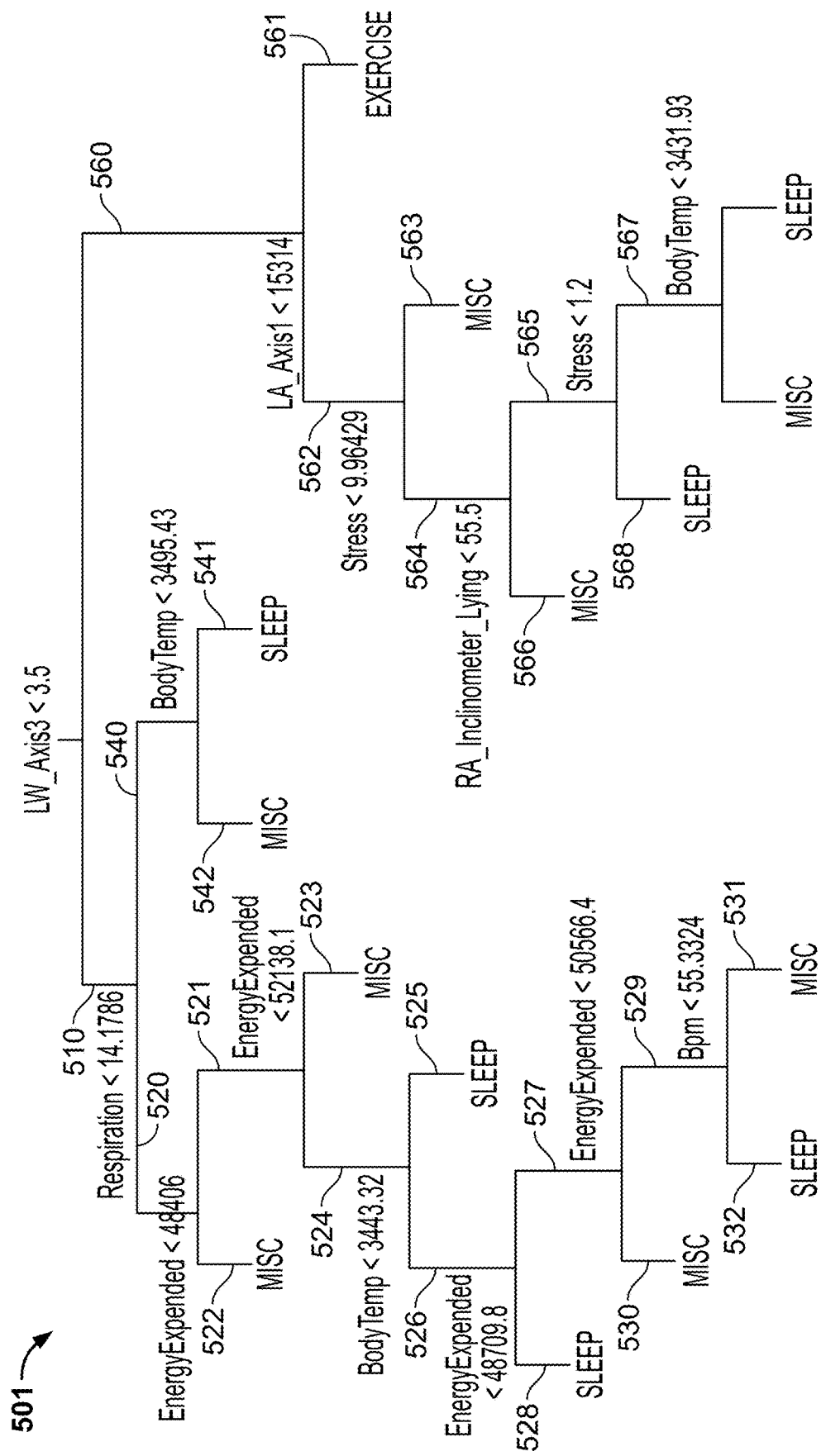
FIGS. 6A and 6B are classification and regression trees (CART) similar to one generated in the experiment of FIGS. 5A and 5B.

FIG. 6A shows a classification and regression tree (CART) 501 similar to the one used for the above-described test. From four ActiGraph devices and the Vital Connect device, the inventors used eight variables ($X_1 \ldots X_8$) (out of about twenty that were recorded and considered), some of which were used more than once, and three subject states ($Y_1 \ldots Y_3$)— EXERCISE, SLEEP, and MISC.

At the top of tree 501 is variable LW_Axis3, which shows left wrist displacement. The decision point calculated was 3.5 "counts," splitting the tree into main branches 510 and 560 to optimize the univariate or multivariate classifications of patient state. ("Counts" are a result of summing post-filtered accelerometer values (raw data at 30 Hz) into epoch "chunks." The value of the counts will vary based on the frequency and intensity of the raw acceleration. The filtering process by which counts are produced may be proprietary to the mHealth device maker.) On main branch 560, variable LA_Axis1, which shows left ankle displacement, was used and the decision point calculated was 15314 counts to determine EXERCISE on branch 561. Variable Stress was used on branch 562 and a decision point of 9.96429% was calculated to determine MISC on branch 563. (Stress may be calculated by the mHealth device based on the ECG sensor data.) On branch 564, variable RA_Inclinometer_Lying (the time lying down (in seconds) during the 1-minute epoch from the right ankle device) was used, and the decision point calculated at 55.5 seconds to determine MISC on branch 566. On branch 565, variable Stress was again used, but this time the decision point was calculated to be 1.2% to determine SLEEP on branch 568. At the bottom of main branch 560 is branch 567, and variable BodyTemp was used to decide between MISC and SLEEP, and the decision point calculated was 34.9193° C. (3491.93 hundredths of a degree Celsius).

Turning to main branch 510, variable Respiration was used and a decision point of 14.1786 breaths per minute was calculated to divide the tree into branches 520 and 540. On branch 540, variable BodyTemp was again used, but this time the decision point was calculated to be 34.9543° C., higher than on branch 565, to decide between MISC 542 and SLEEP 541. On branch 520, variable EnergyExpended (which may also be derived from the ECG sensor data) was used and a decision point of 48406 kCal (kilocalories) was calculated to determine MISC on branch 522. On branch 521, variable EnergyExpended was used again, but a different decision point, calculated to be 52138.1 kCal was used to determine MISC on branch 523. On branch 524, variable BodyTemp was used a third time and a decision point of 34.4332° C. was calculated to determine SLEEP on branch 525. On branch 526, variable EnergyExpended was used a third time and a decision point of 48709.8 kCal was calculated to determine SLEEP on branch 528. On branch 527, variable EnergyExpended was used a fourth time and a decision point of 50566.4 kCal was calculated to determine MISC on branch 530. On branch 529, variable heart rate (bpm) was used and a decision point of 55.3324 beats per minute was calculated to determine SLEEP on branch 532 and MISC on branch 531.

Figure 5B:
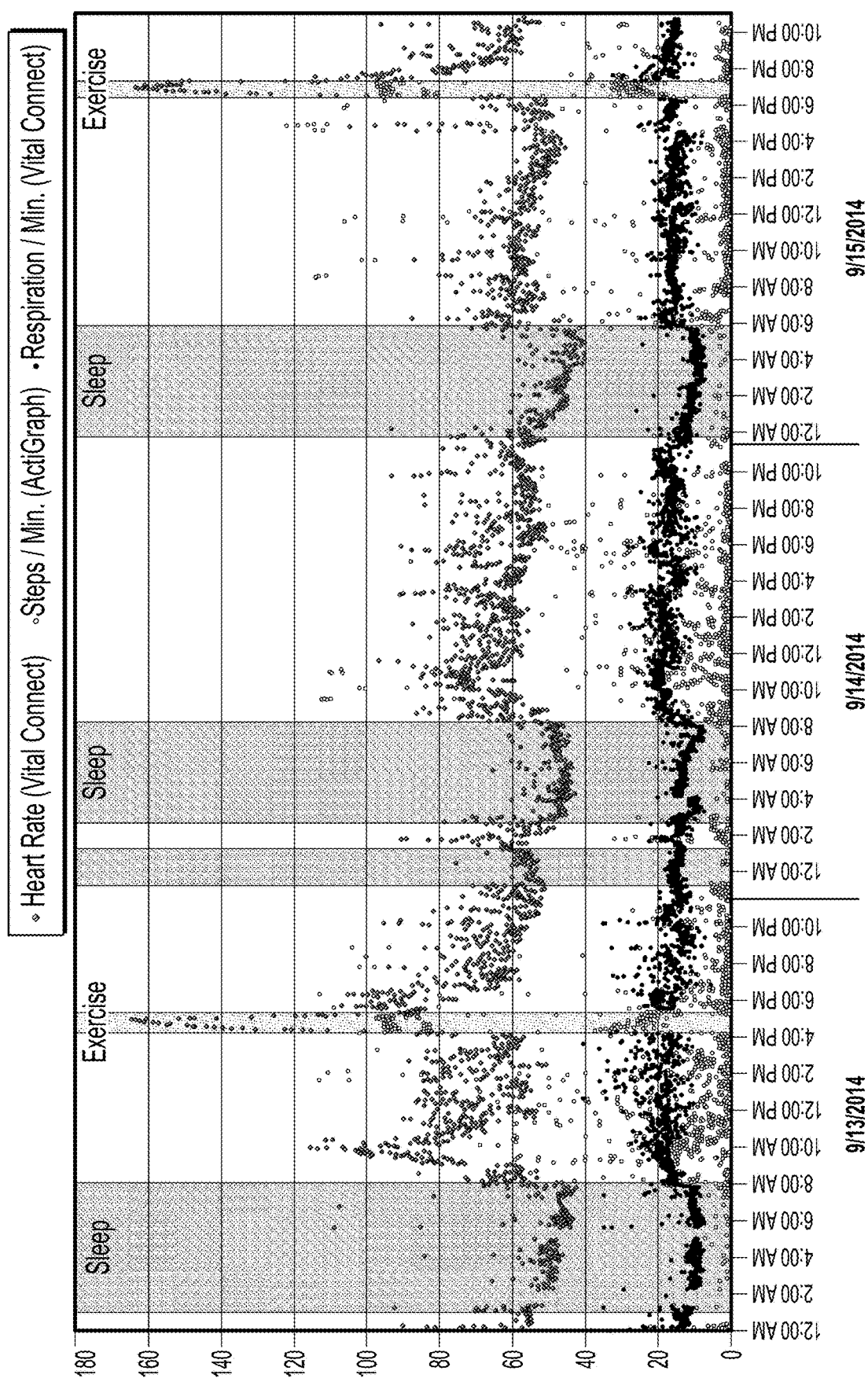
Figure 6B:
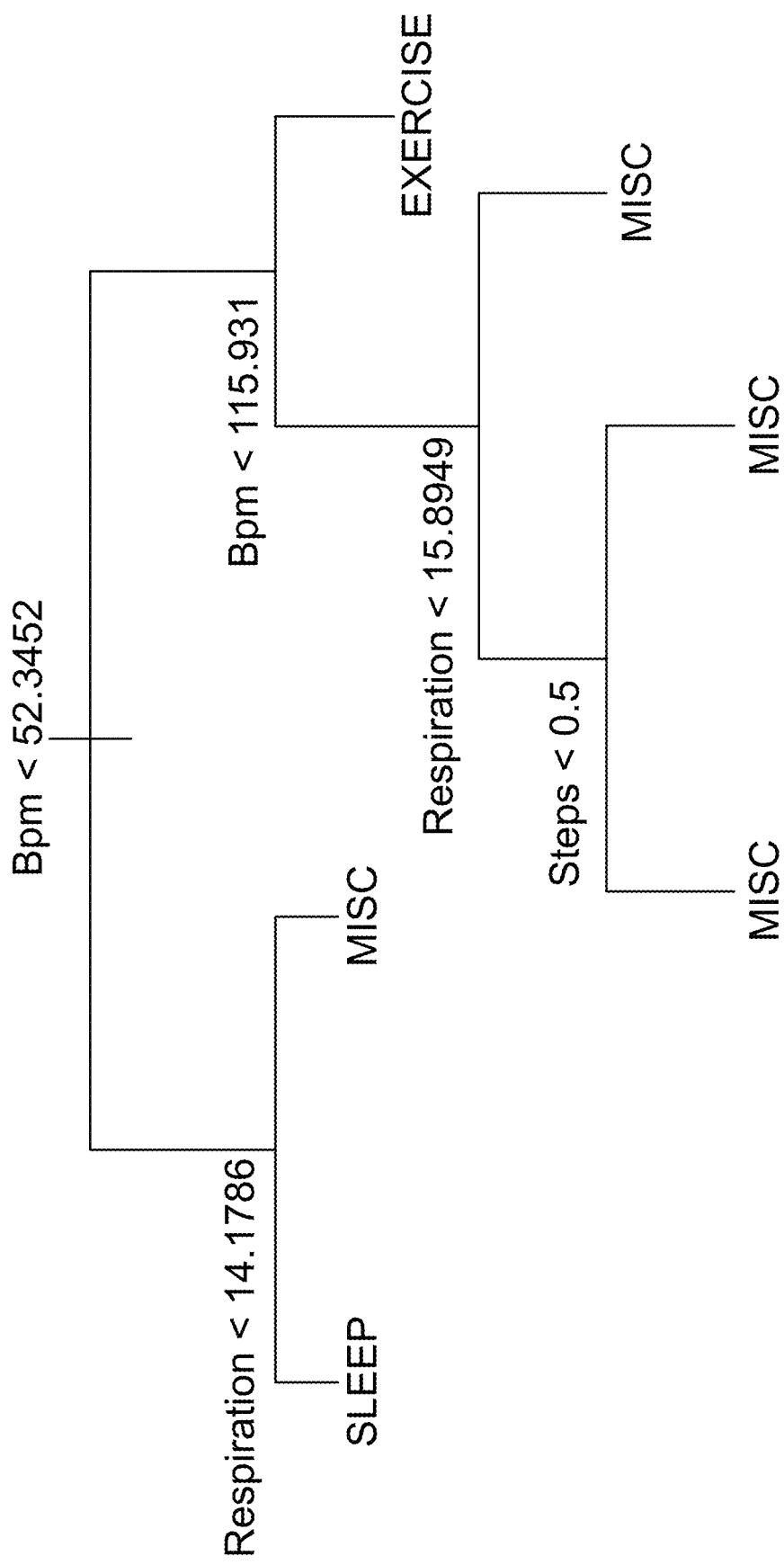

FIG. 6B shows another classification and regression tree (CART) similar to that in FIG. 6A, but with fewer branches, and using only the respiration, heart rate, and steps-per-minute variables shown in FIG. 5B.

The trees in FIGS. 6A and 6B show that variables may be used more than once, even on adjacent branches, to calculate decision points. Since a single variable may contain a wide range of values that may have information about the patient state, a single node in a tree represents a "cut-point" for that variable. The CART algorithm recursively searches for additional cut-points to improve the model predictions for the current variable or any other variable included. The model classification of subject state in the experiment described above was accurate 93% of the time.

The invention has numerous benefits. By detecting or predicting subject state, the invention can be used in pharmacovigilance in clinical trials (activities involving collection of data, assessment, detection, monitoring, and prevention of adverse effects from pharmaceuticals) by alerting monitors or doctors when problems may occur with a drug under test. Currently, the recording of adverse events may not be done in real-time by subjects in a clinical trial, so subjects may record the wrong time (that may not correlate well with the receiving of the drug under test) or may not record the adverse event at all, especially if the event is not severe. Some effects, such as increased stress, may not be noticeable to a subject, but would be detectable by the present invention. The present invention may also be able to obviate the use of a subject diary, thus lessening the burden on clinical trial subjects.

Besides being able to predict subject state, the present invention may be used to further evaluate and distinguish two drugs that otherwise have been shown to possess the same overall efficacy. For example, while two oncology drugs may both be proven efficacious for reducing tumor size, quality-of-life factors such as nausea, headache, minor pain, and general activity or energy levels, if omitted from those efficacy determinations (as non-serious adverse events, and/or as derived from insufficiently accurate and reliable data), would be clinically useful and valuable to patients and clinical trial sponsors alike. On the basis of the accurate, reliable mHealth data provided by the present invention, sponsors may be able to refine drug product labeling, gather support for additional indications, and improve adverse event tracking across phases (including post-approval) and therapeutic areas.

Moreover, the present invention may help address the problem of omitted variables recorded during a clinical trial, an example of which is exercise frequency and duration. Such variables may not be tracked currently, and they may have an effect on the efficacy of a drug under test, yet that information currently does not get analyzed. In addition, the invention may prevent (or reduce) or detect fraud or misrecording of information during a clinical trial Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

Referring back to the block diagrams of systems for determining a subject's state utilizing data received from multiple mobile health devices shown in FIGS. 1A, 1B, and 3, systems 10 and 300 may include a processor and have an internal or external memory for storing data and programs. A general-purpose computer may include a central processing unit (CPU) for executing instructions in response to commands and a communication device for sending and receiving data.

In one embodiment, the integrated data and predictive model may be transmitted over a network, which may include a communications interface that allows software and data to be transferred between client device, processor, the other system components, and the external systems, such as mobile health devices and EDC systems. In this specification, the terms "computer program medium" and "computer readable medium" are generally used to refer to media such as a removable storage device, a disk capable of installation in a disk drive, and signals on a channel. These computer program products may provide software or program instructions to a computer system.

Computer programs that may be associated with applications of the system for determining subject states in mobile health (called "computer control logic") may be stored in the main memory or secondary memory. Such computer programs may also be received via a communications interface. Such computer programs, when executed, may enable the computer system to perform the features as discussed herein. In particular, the computer programs, when executed, may enable the processor to perform the described techniques. Accordingly, such computer programs may represent controllers of the computer system.

In one embodiment, the computer-based methods may be accessed or implemented over the World Wide Web by providing access via a Web Page to the methods described herein. Accordingly, the Web Page may be identified by a URL. The URL may denote both a server and a particular file or page on the server. In this embodiment, it is envisioned that a client computer system may interact with a browser to select a particular URL, which in turn may cause the browser to send a request for that URL or page to the server identified in the URL. Typically, the server may respond to the request by retrieving the requested page and transmitting the data for that page back to the requesting client computer system (the client/server interaction may be typically performed in accordance with the hypertext transport protocol or HTTP). The selected page may then be displayed to the user on the client's display screen. The client may then cause the server containing a computer program to launch an application, for example, to perform an analysis according to the described techniques. In another implementation, the server may download an application to be run on the client to perform an analysis according to the described techniques.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-implemented method comprising:
receiving data during time intervals from a plurality of mobile health sensors, including sensors within a single device or multiple devices;
receiving a diary that records subject state determinations;
integrating the data from the mobile health sensors and the subject state determinations from the diary;
cleaning the integrated data;
determining which variables optimally predict the subject state;
partitioning said integrated and cleaned data using a combination of ranges of values for the variables that optimally predict the subject state;
generating a training set of data comprising a portion of the integrated, cleaned, and partitioned data;
training a predictive model using the training set and a machine learning algorithm; and
generating the predictive model of the state of the subject of the clinical trial based on the training set; and
using the predictive model to determine subject state for data without the diary that records said subject state determination,
wherein the subject state comprises a digital bio-marker for a disease condition, and wherein to determine the ranges of the values for the variables that optimally predict the subject state, the method further comprises:
(a) for a first variable $X_1$, using a range of data, $X_1 > A$, where A is a defined value, to classify the data according to a first state $Y_1$ and a second state $Y_2$;
(b) computing a ratio between $Y_1$ and $Y_2$, or between $Y_1$ and $Y_1+Y_2$, for data where $X_1$ is not greater than A and for data where $X_1$ is greater than A, respectively; and iteratively repeating (a) and (b) for selected values of A to maximize said ratio between $Y_1$ and $Y_2$, or between $Y_1$ and $Y_1+Y_2$.

2. The method of claim 1, further comprising:
classifying a combination of ranges of value for variables received from the mobile health sensors; and
testing a second portion of the integrated and cleaned data using the predictive model and comparing the predicted subject states against the subject state determinations from the diary that records said subject state determinations.

3. The method of claim 2, wherein to generate the training set of data comprising the portion of the integrated, cleaned, and partitioned data, the method further comprises randomly separating the integrated, cleaned, and partitioned data into said portion and said second portion based on a predetermined percentage.

4. The method of claim 1, further comprising:
integrating new data that are input;
cleaning the integrated new data; and
receiving the predictive model and the cleaned data and determining a subject state.

5. The method of claim 1, further comprising receiving data from a user in addition to the plurality of sensors.

6. The method of claim 1, further comprising calculating time intervals in which to collect an optimal amount of data to predict a state of a subject in a clinical trial.

7. The method of claim 1, wherein the disease condition is an arrhythmia.

8. The method of claim 1, further comprising:
(c) for a second variable $X_2$, using a range of data, $X_2 > F$, where F is a defined value, to classify the data according to the first state $Y_1$ and the second state $Y_2$;
(d) computing a ratio between $Y_1$ and $Y_2$, or between $Y_1$ and $Y_1+Y_2$, for data where $X_2$ is not greater than F and for data where $X_2$ is greater than F, respectively; and iteratively repeating (c) and (d) for selected values of F to maximize said ratio between $Y_1$ and $Y_2$, or between $Y_1$ and $Y_1+Y_2$.

9. The method of claim 1, wherein the predictive model represents subject state as a function of multiple variables $X_n$, which represent clinical data, the variables $X_n$ including at least a plurality of: heart rate, electrocardiogram, body temperature, skin temperature, movement, and blood pressure.

* * * * *